United States Patent [19]

Koizumi et al.

[11] Patent Number: 5,395,766
[45] Date of Patent: Mar. 7, 1995

[54] OPTICALLY ACTIVE TRANS-2-ARYL-1-CYCLOHEXANOL DERIVATIVES AND A PROCESS FOR PRODUCING THE COMPOUNDS

[75] Inventors: Yasuyuki Koizumi; Naoyuki Yoshida; Teruyo Sugiura; Kazutoshi Miyazawa, all of Ichihara, Japan

[73] Assignee: Chisso Corporation, Osaka, Japan

[21] Appl. No.: 968,311

[22] Filed: Oct. 29, 1992

[30] Foreign Application Priority Data

Jan. 11, 1991 [JP] Japan ................... 3-313092

[51] Int. Cl.⁶ .................... C07D 315/00; C07C 69/00; C07C 41/00
[52] U.S. Cl. ..................................... 435/280; 579/421; 560/129; 568/49; 568/633; 568/644
[58] Field of Search ................ 549/421; 568/644, 633, 568/49; 560/129; 435/280

[56] References Cited

U.S. PATENT DOCUMENTS

| | | | |
|---|---|---|---|
| 2,130,525 | 9/1938 | Coleman et al. | 568/644 |
| 4,400,293 | 8/1983 | Römer et al. | 568/644 |
| 4,654,162 | 3/1987 | Sugiwari et al. | 568/644 |

Primary Examiner—C. Warren Ivy
Assistant Examiner—Raymond Covington
Attorney, Agent, or Firm—Wenderoth, Lind & Ponack

[57] ABSTRACT

The present invention provides an optically active trans-2-aryl-1-cyclohexanol derivative represented by the following general formula (I).

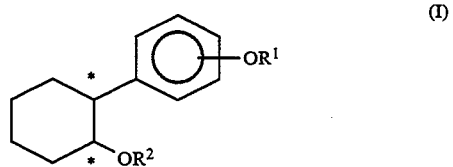

(I)

The compounds can be obtained by transesterifiation reaction of the following compound (II) as a starting material with lipase.

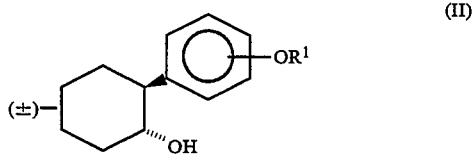

(II)

The optically active trans-2-aryl-1-cyclohexanol derivative can be used as an asymmetric source of asymmetric Diels-Alder reaction or a starting material of physiological active materials.

2 Claims, No Drawings

OPTICALLY ACTIVE TRANS-2-ARYL-1-CYCLOHEXANOL DERIVATIVES AND A PROCESS FOR PRODUCING THE COMPOUNDS

BACKGROUND OF THE INVENTION

1. Field of the Invention

The present invention relates to optically active trans-2-aryl-1-cyclohexanol derivatives and a process for production thereof.

2. Description of the Prior Art

Racemic trans-2-aryl 1-cyclohexanol derivatives such as trans-2- (2-benzyloxyphenyl) -1 -cyclohexanol are known as synthetic materials for several types of aminopropanol. However, the optically active compounds are not yet known (DE3427241), and these compounds are new compounds which are synthesized for the first time by the inventors of the present invention.

It is known that conventionally known optically active trans-2-phenyl-1-cyclohexanol, which is a similar compound for the compounds of the present invention, is useful as an asymmetric source of asymmetric Diels-Alder reaction. For example, Green et al. synthesized (-)-α-and (+)-β-Cuperenone (J. Am. Chem, Soc., 109, 4752(1987)).

The compounds of the present invention are naturally useful as the asymmetric source of asymmetric Diels-Alder reaction, considering the steric configuration, higher asymmetric yield will be expected than that of optically active trans-2-phenyl-1-cyclohexanol. Moreover, the compounds of the present invention will be expected not only to be useful asymmetric sources but also as useful starting materials for synthesizing physiological active materials by using the skeleton.

Namely, the skeleton represented by R¹ in the general formula (I) of the compounds of the present invention acts as a protective group for a phenolic hydroxyl group and has wide selectivity of functional groups. The hydroxyl group on the cyclohexane ring also has the same characteristics. The compounds have two hydroxyl groups in a molecule, so that it will be expected to use them widely in comparison with known optically active trans-2-phenyl-1-cyclohexanol.

As an example of the compounds of the present invention, 2- (2-benzyloxyphenyl)-1-cyclohexanol (a compound described in Example 2) is useful as a starting material of RG-1 2915 which is a pharmaceutical as shown in the following flow chart (U.S. Pat. No. 5,086,179).

Namely, after a hydroxy group is introduced into a deprotected group (for example, a mesyloxy group), a benzyl group is deprotected by catalytic reduction, and intramolecular cyclization can be conducted by nucleophilic reaction. Then, the resulting compound is treated by chlorination, acylation and haloform reaction to introduce a carboxy group into the benzene skeleton, and a principle skeleton can be obtained. Finally, 3-aminoquinuclidine is reacted with the obtained compound to form an acid-amide bond, and RG-1291 5 can be obtained.

RG-1 2915 exhibits 5HT3-antagonist properties including unique CNS (center nervous system), antiemeric and gastric prokinetic activity, and is void of any significant D₂ receptor binding affinity.

Further, it is known that only one of the optical isomers of the compounds has good activity. Accordingly, the steric configuration of the starting materials is very important.

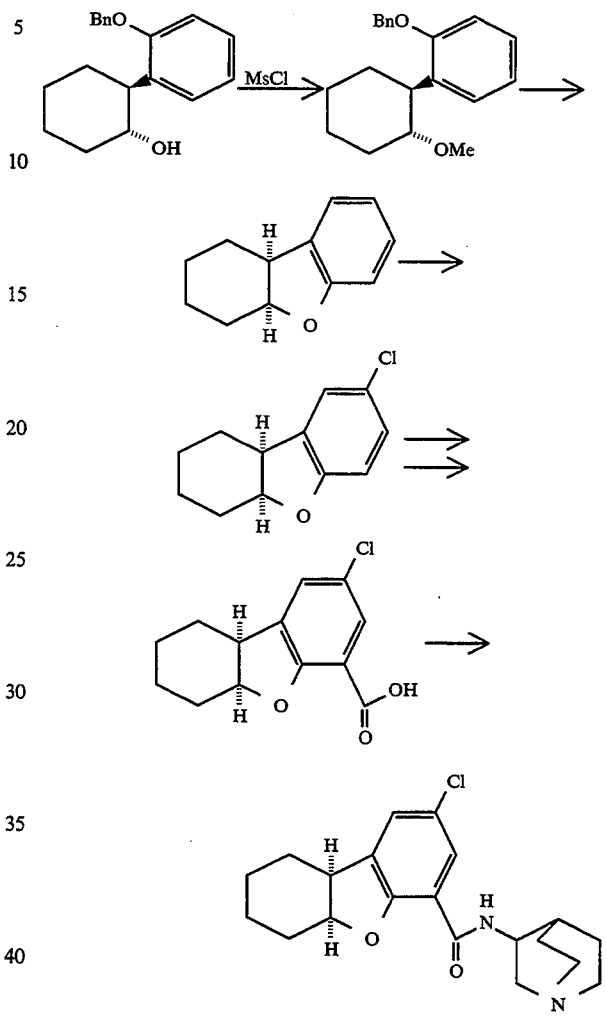

For synthesizing optically active trans-2-phenyl-1cyclohexanol which is similar to the compounds of the present invention, an optical resolution method using transesterification of enzymes disclosed by Yoshida et al., Japanese Patent Application No. 1-209958(1989), an asymmetric hydroboration method reported by Brown et al., J. Org. Chem., 47, 5074(1982) etc., an optical resolution method using hydrobytic action of an enzyme described by Robert et al., Chimia, 40, 318(1986) and the like are known. These methods can be conceived by a person having ordinary skill in the art to which said subject matter pertains to synthesize the compounds of the present invention.

The process of the present invention looks like the application of the method disclosed by Yoshida et al. at first glance. However, a distinction should be drawn between the process of the present invention and the method of Yoshida et al., because different substrates are used, although a similar technique using enzymes is adopted.

The reason is as follows. For example, asymmetric reduction of β-ketoesters by using baker's yeast is well-known. In the reduction of ethyl acetoacetate, the optical yield is 90% ee (Zeebach et al., Helv. Chim. Acta, 60, 1175(1 977)), while in the case of ethyl propionylacetate, the optical yield is only 40% ee (Fleiter et al., Helv. Chim. Acta, 62, 2829(1 979)). Further, in the case of γ-chloroeacetoacetic acid ester wherein an alkyl group of the ester is pentyl, the optical yield is about 0% ee, while the optical yield is more than 95% ee in a hexyl group and alkyl groups having more than 7 carbon atoms (Seen et al., J. Am. Chem. Soc., 105, 5925(1983)). Accordingly, the yield is remarkably changed according to substrates.

Similarly, in the method of asymmetric synthesis, it is very difficult to anticipate change of the yield according to substrates, so that the possibility of the application to the compounds of the present invention is found for the first time by trial and error.

As described above, it is desired to develop a method for efficiently obtaining in large quantities optically active trans-2-aryl-1-cyclohexanol derivatives useful as starting materials for physiologically active materials and having wide application to the asymmetric synthesis.

The inventors of the present invention conducted research for resolving the above problems and then successfully obtained optically active trans-2-aryl-1-cyclohexanol derivatives.

SUMMARY OF THE INVENTION

Namely, the present invention provides optically active trans-2-aryl-1-cyclohexanol derivatives represented by the general formula (I):

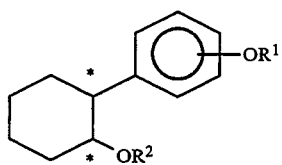

(I)

wherein $R^1$ is hydrogen, alkyl of 1–15 carbon atoms, methoxymethyl, methoxyethyl, methylthio methyl, tetrahydropyranyl, cyclopropylmethyl, allyl, cyclohexyl, benzyl, 9-anthrylmethyl or t-butyldimethylsilyl, $R^2$ is hydrogen or acyl of 1–15 carbon atoms, and * shows an asymmetric carbon atom.

The second invention is a process for producing optically active trans-2-aryl-1-cyclohexanol derivatives characterized in that it comprises reacting a fatty acid vinyl ester or a triglyceride with (+)-trans-2-aryl-1-cyclohexanol represented by the general formula (II):

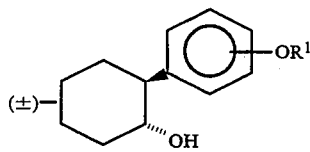

(II)

wherein $R^1$ is hydrogen, alkyl of 1–15 carbon atoms, methoxymethyl, methoxyethyl, methylthiomethyl, tetrahydropyranyl, cyclopropylmethyl, allyl, cyclohexyl, benzyl, 9-anthrylmethyl or t-butyldimethylsilyl, in the presence of an esterase to effect the transesterification reaction.

The third invention is a process for producing optically active trans-2-aryl-1-cyclohexanols characterized in that it comprises hydrolyzing optically active trans-2-aryl-1-acyloxycyclohexanes.

The optically active trans-2-aryl-1-cyclohexanol derivatives of the present invention are represented by the said general formula (I), the following compounds are exemplified.

(1S, 2R)-trans-2-(2-hydroxyphenyl)-1-cyclohexanol,
(1S, 2R)-trans-2-(3-hydroxyphenyl)-1-cyclohexanol,
(1S, 2R)-trans-2-(4-hydroxyphenyl)-1-cyclohexanol,
(1S, 2R)-trans-2-(2-methoxyphenyl)-1-cyclohexanol,
(1S, 2R)-trans-2-(3-methoxyphenyl)-1-cyclohexanol,
(1S, 2R)-trans-2-(4-methoxyphenyl)-1-cyclohexanol,
(1S, 2R)-trans-2-(2-ethoxyphenyl)-1-cyclohexanol,
(1S, 2R)-trans-2-(3-ethoxyphenyl)-1-cyclohexanol,
(1S, 2R)-trans-2-(4-ethoxyphenyl)-1-cyclohexanol,
(1S, 2R)-trans-2-(2-propyloxyphenyl)-1-cyclohexanol,
(1S, 2R)-trans-2-(3-propyloxyphenyl)-1-cyclohexanol,
(1S, 2R)-trans-2-(4-propyloxyphenyl)-1-cyclohexanol,
(1S, 2R)-trans-2-(2-isopropyloxyphenyl)-1-cyclohexanol,
(1S, 2R)-trans-2-(3-isopropyloxyphenyl)-1-cyclohexanol,
(1S, 2R)-trans-2-(4-isopropyloxyphenyl)-1-cyclohexanol,
(1S, 2R)-trans-2-(2-butoxyphenyl)-1-cyclohexanol,
(1S, 2R)-trans-2-(3-butoxyphenyl)-1-cyclohexanol,
(1S, 2R)-trans-2-(4-butoxyphenyl)-1-cyclohexanol,
(1S, 2R)-trans-2-(2-sec-butoxyphenyl)-1-cyclohexanol,
(1S, 2R)-trans-2-(3-sec-butoxyphenyl)-1-cyclohexanol,
(1S, 2R)-trans-2-(4-sec-butoxyphenyl)-1-cyclohexanol,
(1S, 2R)-trans-2-(2-tert-butoxyphenyl)-1-cyclohexanol,
(1S, 2R)-trans-2-(3-tert-butoxyphenyl)-1-cyclohexanol,
(1S, 2R)-trans-2-(4-tert-butoxyphenyl)-1-cyclohexanol,
(1S, 2R)-trans-2-(2-methoxymethyloxyphenyl)-1-cyclohexanol,
(1S, 2R)-trans-2-(3-methoxymethyloxyphenyl)-1-cyclohexanol,
(1S, 2R)-trans-2-(4-methoxymethyloxyphenyl)-1-cyclohexanol,
(1S, 2R)-trans-2-(2-methoxyethoxymethyloxyphenyl)-1-cyclohexanol,
(1S, 2R)-trans-2-(3-methoxyethoxymethyloxyphenyl)-1-cyclohexanol,
(1S, 2R)-trans-2-(4-methoxyethoxymethyloxyphenyl)-1-cyclohexanol,
(1S, 2R)-trans-2-(2-methylthiomethyloxyphenyl)-1-cyclohexanol,
(1S, 2R)-trans-2-(3-methylthiomethyloxyphenyl)-1-cyclohexanol,
(1S, 2R)-trans-2-(4-methylthiomethyloxyphenyl)-1-cyclohexanol,
(1S, 2R)-trans-2-(2-tetrahydropyranyloxyphenyl)-1-cyclohexanol,
(1S, 2R)-trans-2-(3-tetrahydropyranyloxyphenyl)-1-cyclohexanol,
(1S, 2R)-trans-2-(4-tetrahydropyranyloxyphenyl)-1-cyclohexanol,
(1S, 2R)-trans-2-(2-cyclopropylmethyloxyphenyl)-1-cyclohexanol,
(1S, 2R)-trans-2-(3-cyclopropylmethyloxyphenyl)-1-cyclohexanol, (1S, 2R)-trans-2-(4-cyclopropylmethyloxyphenyl)-1-cyclohexanol,
(1S, 2R)-trans-2-(2-cyclohexyloxyphenyl)-1-cyclohexanol,
(1S, 2R)-trans-2-(3-cyclohexyloxyphenyl)-1-cyclohexanol,
(1S, 2R)-trans-2-(4-cyclohexyloxyphenyl)-1-cyclohexanol,
(1S, 2R)-trans-2-(2-allyloxyphenyl)-1-cyclohexanol,
(1S, 2R)-trans-2-(3-allyloxyphenyl)-1-cyclohexanol,
(1S, 2R)-trans-2-(4-allyloxyphenyl)-1-cyclohexanol,
(1S, 2R)-trans-2-(2-benzyloxyphenyl)-1-cyclohexanol,
(1S, 2R)-trans-2-(3-benzyloxyphenyl)-1-cyclohexanol,
(1S, 2R)-trans-2-(4-benzyloxyphenyl)-1-cyclohexanol,
(1S, 2R)-trans-2-(2-(9-anthrylmethyloxy)phenyl)-1-cyclohexanol,
(1S, 2R)-trans-2-(3-(9-anthrylmethyloxy)phenyl)-1-cyclohexanol,
(1S, 2R)-trans-2-(4-(9-anthrylmethyloxy)phenyl)-1-cyclohexanol,
(1S, 2R)-trans-2-(2-tert-butyldimethylsilyloxyphenyl)-1-cyclohexanol,
(1S, 2R)-trans-2-(3-tert-butyldimethylsilyloxyphenyl)-1-cyclohexanol,
(1S, 2R)-trans-2-(4-tert-butyldimethylsilyloxyphenyl)-1-cyclohexanol,
(1S, 2R)-trans-2-(2-methoxyphenyl)-1-acetyloxycyclohexane,
(1S, 2R)-trans-2-(3-methoxyphenyl)-1-acetyloxycyclohexane,
(1S, 2R)-trans-2-(4-methoxyphenyl)-1-acetyloxycyclohexane,
(1S, 2R)-trans-2-(2-ethoxyphenyl)-1-acetyloxycyclohexane,
(1S, 2R)-trans-2-(3-ethoxyphenyl)-1-acetyloxycyclohexane,
(1S, 2R)-trans-2-(4-ethoxyphenyl)-1-acetyloxycyclohexane,
(1S, 2R)-trans-2-(2-propyloxyphenyl)-1-acetyloxycyclohexane,
(1S, 2R)-trans-2-(3-propyloxyphenyl)-1-acetyloxycyclohexane,
(1S, 2R)-trans-2-(4-propyloxyphenyl)-1-acetyloxycyclohexane,
(1S, 2R)-trans-2-(2-isopropyloxyphenyl)-1-acetyloxycyclohexane,
(1S, 2R)-trans-2-(3-isopropyloxyphenyl)-1-acetyloxycyclohexane,
(1S, 2R)-trans-2-(4-isopropyloxyphenyl)-1-acetyloxycyclohexane,
(1S, 2R)-trans-2-(2-isopropyloxyphenyl)-1-acetyloxycyclohexane,
(1S, 2R)-trans-2-(3-isopropyloxyphenyl)-1-acetyloxycyclohexane,
(1S, 2R)-trans-2-(4-isopropyloxyphenyl)-1-acetyloxycyclohexane,
(1S, 2R)-trans-2-(2-butoxyphenyl)-1-acetyloxycyclohexane,
(1S, 2R)-trans-2-(3-butoxyphenyl)-1-acetyloxycyclohexane,
(1S, 2R)-trans-2-(4-butoxyphenyl)-1-acetyloxycyclohexane,
(1S, 2R)-trans-2-(2-sec-butoxyphenyl)-1-acetyloxycyclohexane,
(1S, 2R)-trans-2-(3-sec-butoxyphenyl)-1-acetyloxycyclohexane,
(1S, 2R)-trans-2-(4-sec-butoxyphenyl)-1-acetyloxycyclohexane,
(1S, 2R)-trans-2-(2-tert-butoxyphenyl)-1-acetyloxycyclohexane,
(1S, 2R)-trans-2-(3-tert-butoxyphenyl)-1-acetyloxycyclohexane,
(1S, 2R)-trans-2-(4-tert-butoxyphenyl)-1-acetyloxycyclohexane,
(1S, 2R)-trans-2-(2-methoxymethyloxyphenyl)-1-acetyloxycyclohexane,
(1S, 2R)-trans-2-(3-methoxymethyloxyphenyl)-1-acetyloxycyclohexane,
(1S, 2R)-trans-2-(4-methoxymethyloxyphenyl)-1-acetyloxycyclohexane,
(1S, 2R)-trans-2-(2-methoxyethoxymethyloxyphenyl)-1-acetyloxycyclohexane,
(1S, 2R)-trans-2-(3-methoxyethoxymethyloxyphenyl)-1-acetyloxycyclohexane,
(1S, 2R)-trans-2-(4-methoxyethoxymethyloxyphenyl)-1-acetyloxycyclohexane,
(1S, 2R)-trans-2-(2-methylthiomethyloxyphenyl)-1-acetyloxycyclohexane,
(1S, 2R)-trans-2-(3-methylthiomethyloxyphenyl)-1-acetyloxycyclohexane,
(1S, 2R)-trans-2-(4-methylthiomethyloxyphenyl)-1-acetyloxycyclohexane,
(1S, 2R)-trans-2-(2-tetrahydropyranyloxyphenyl)-1-acetyloxycyclohexane,
(1S, 2R)-trans-2-(3-tetrahydropyranyloxyphenyl)-1-acetyloxycyclohexane,
(1S, 2R)-trans-2-(4-tetrahydropyranyloxyphenyl)-1-acetyloxycyclohexane,
(1S, 2R)-trans-2-(2-cyclopropylmethyloxyphenyl)-1-acetyloxycyclohexane,
(1S, 2R)-trans-2-(3-cyclopropylmethyloxyphenyl)-1-acetyloxycyclohexane,
(1S, 2R)-trans-2-(4-cyclopropylmethyloxyphenyl)-1-acetyloxycyclohexane,
(1S, 2R)-trans-2-(2-cyclohexyloxyphenyl)-1-acetyloxycyclohexane,
(1S, 2R)-trans-2-(3-cyclohexyloxyphenyl)-1-acetyloxycyclohexane,
(1S, 2R)-trans-2-(4-cyclohexyloxyphenyl)-1-acetyloxycyclohexane,
(1S, 2R)-trans-2-(2-allyloxyphenyl)-1-acetyloxycyclohexane,
(1S, 2R)-trans-2-(3-allyloxyphenyl)-1-acetyloxycyclohexane,
(1S, 2R)-trans-2-(4-allyloxyphenyl)-1-acetyloxycyclohexane,
(1S, 2R)-trans-2-(2-benzyloxyphenyl)-1-acetyloxycyclohexane,
(1S, 2R)-trans-2-(3-benzyloxyphenyl)-1-acetyloxycyclohexane,
(1S, 2R)-trans-2-(4-benzyloxyphenyl)-1-acetyloxycyclohexane,
(1S, 2R)-trans-2-(2-(9-anthrylmethyloxy)phenyl)-1-acetyloxycyclohexane,
(1S, 2R)-trans-2-(3-(9-anthrylmethyloxy)phenyl)-1-acetyloxycyclohexane,
(1S, 2R)-trans-2-(4-(9-anthrylmethyloxy)phenyl)-1-acetyloxycyclohexane,
(1S, 2R)-trans-2-(2-tert-butyldimethylsilyloxyphenyl)-1-acetyloxycyclohexane,
(1S, 2R)-trans-2-(3-tert-butyldimethylsilyloxyphenyl)-1-acetyloxycyclohexane, (1S, 2R)-trans-2-(4-tert-butyldimethylsilyloxyphenyl)-1-acetyloxycyclohexane,
(1S, 2R)-trans-2-(2-methoxyphenyl)-1-propanoyloxycyclohexane,
(1S, 2R)-trans-2-(3-methoxyphenyl)-1-propanoyloxycyclohexane,
(1S, 2R)-trans -2-(4-methoxypheny)-1-propanoyloxycyclohexane,
(1S, 2R)-trans-2-(2-ethoxyphenyl)-1-propanoyloxycyclohexane,
(1S, 2R)-trans-2-(3-ethoxyphenyl)-1-propanoyloxycyclohexane,
(1S, 2R)-trans-2-(4-ethoxyphenyl)-1-propanoyloxycyclohexane,
(1S, 2R)-trans-2-(2-propyloxyphenyl)-1-propanoyloxycyclohexane,
(1S, 2R)-trans-2-(3-propyloxyphenyl)-1-propanoyloxycyclohexane,
(1S, 2R)-trans-2-(4-propyloxyphenyl)-1-propanoyloxycyclohexane,
(1S, 2R)-trans-2-(2-isopropyloxyphenyl)-1-propanoyloxycyclohexane,
(1S, 2R)-trans-2-(3-isopropyloxyphenyl)-1-propanoyloxycyclohexane,
(1S, 2R)-trans-2-(4-isopropyloxyphenyl)-1-propanoyloxycyclohexane,
(1S, 2R)-trans-2-(2-isopropyloxyphenyl)-1-propanoyloxycyclohexane,
(1S, 2R)-trans-2-(3-isopropyloxyphenyl)-1-propanoyloxycyclohexane,
(1S, 2R)-trans-2-(4-isopropyloxyphenyl)-1-propanoyloxycyclohexane,
(1S, 2R)-trans-2-(2-butoxyphenyl)-1-propanoyloxycyclohexane,
(1S, 2R)-trans-2-(3-butoxyphenyl)-1-propanoyloxycyclohexane,
(1S, 2R)-trans-2-(4-butoxyphenyl)-1-propanoyloxycyclohexane,
(1S, 2R)-trans-2-(2-sec-butoxyphenyl)-1-propanoyloxycyclohexane,
(1S, 2R)-trans-2-(3-sec-butoxyphenyl)-1-propanoyloxycyclohexane,
(1S, 2R)-trans-2-(4-sec-butoxyphenyl)-1-propanoyloxycyclohexane,
(1S, 2R)-trans-2-(2-tert-butoxyphenyl)-1-propanoyloxycyclohexane,
(1S, 2R)-trans-2-(3-tert-butoxyphenyl)-1-propanoyloxycyclohexane,
(1S, 2R)-trans-2-(4-tert-butoxyphenyl)-1-propanoyloxycyclohexane,
(1S, 2R)-trans-2-(2-methoxymethyloxyphenyl)-1-propanoyloxycyclohexane,
(1S, 2R)-trans-2-(3-methoxymethyloxyphenyl)-1-propanoyloxycyclohexane,
(1S, 2R)-trans-2-(4-methoxymethyloxyphenyl)-1-propanoyloxycyclohexane,
(1S, 2R)-trans-2-(2-methoxyethoxymethyloxyphenyl)-1-propanoyloxycyclohexane,
(1S, 2R)-trans-2-(3-methoxyethoxymethyloxyphenyl)-1-propanoyloxycyclohexane,
(1S, 2R)-trans-2-(4-methoxyethoxymethyloxyphenyl)-1-propanoyloxycyclohexane,
(1S, 2R)-trans-2-(2-methylthiomethyloxyphenyl)-1-propanoyloxycyclohexane,
(1S, 2R)-trans-2-(3-methylthiomethyloxyphenyl)-1-propanoyloxycyclohexane,
(1S, 2R)-trans-2-(4-methylthiomethyloxyphenyl)-1-propanoyloxycyclohexane,
(1S, 2R)-trans-2-(2-tetrahydropyranyloxyphenyl)-1-propanoyloxycyclohexane,
(1S, 2R)-trans-2-(3-tetrahydropyranyloxyphenyl)-1-propanoyloxycyclohexane,
(1S, 2R)-trans-2-(4-tetrahydropyranyloxyphenyl)-1-propanoyloxycyclohexane,
(1S, 2R)-trans-2-(2-cyclopropylmethyloxyphenyl)-1-propanoyloxycyclohexane,
(1S, 2R)-trans-2-(3-cyclopropylmethyloxyphenyl)-1-propanoyloxycyclohexane,
(1S, 2R)-trans-2-(4-cyclopropylmethyloxyphenyl)-1-propanoyloxycyclohexane,
(1S, 2R)-trans-2-(2-cyclohexyloxyphenyl)-1-propanoyloxycyclohexane,
(1S, 2R)-trans-2-(3-cyclohexyloxyphenyl)-1-propanoyloxycyclohexane,
(1S, 2R)-trans-2-(4-cyclohexyloxyphenyl)-1-propanoyloxycyclohexane,
(1S, 2R)-trans-2-(2-allyloxyphenyl)-1-propanoyloxycyclohexane,
(1S, 2R)-trans-2-(3-allyloxyphenyl)-1-propanoyloxycyclohexane,
(1S, 2R)-trans-2-(4-allyloxyphenyl)-1-propanoyloxycyclohexane,
(1S, 2R)-trans-2-(2-benzyloxyphenyl)-1-propanoyloxycyclohexane,
(1S, 2R)-trans-2-(3-benzyloxyphenyl)-1-propanoyloxycyclohexane,
(1S, 2R)-trans-2-(4-benzyloxyphenyl)-1-propanoyloxycyclohexane,
(1S, 2R)-trans-2-(2-(9-anthrylmethyloxy)phenyl)-1-propanoyloxycyclohexane,
(1S, 2R)-trans-2-(3-(9-anthrylmethyloxy)phenyl)-1-propanoyloxycyclohexane,
(1S, 2R)-trans-2-(4-(9-anthrylmethyloxy)phenyl)-1-propanoyloxycyclohexane,
(1S, 2R)-trans-2-(2-tert-butyldimethylsilyloxyphenyl)-1-propanoyloxycyclohexane,
(1S, 2R)-trans-2-(3-tert-butyldimethylsilyloxyphenyl)-1-propanoyloxycyclohexane,
(1S, 2R)-trans-2-(4-tert-butyldimethylsilyloxyphenyl)-1-propanoyloxycyclohexane,
(1S, 2R)-trans-2-(2-methoxyphenyl)-1-hexanoyloxycyclohexane,
(1S, 2R)-trans-2-(3-methoxyphenyl)-1-hexanoyloxycyclohexane,
(1S, 2R)-trans-2-(4-methoxyphenyl)-1-hexanoyloxycyclohexane,
(1S, 2R)-trans-2-(2-ethoxyphenyl)-1-hexanoyloxycyclohexane,
(1S, 2R)-trans-2-(3-ethoxyphenyl)-1-hexanoyloxycyclohexane,
(1S, 2R)-trans-2-(4-ethoxyphenyl)-1-hexanoyloxycyclohexane,
(1S, 2R)-trans-2-(2-propyloxyphenyl)-1-hexanoyloxycyclohexane,
(1S, 2R)-trans-2-(3-propyloxyphenyl)-1-hexanoy loxycyclohexane,
(1S, 2R)-trans-2-(4-propyloxyphenyl)-1-hexanoyloxycyclohexane,
(1S, 2R)-trans-2-(2-isopropyloxyphenyl)-1-hexanoyloxycyclohexane,
(1S, 2R)-trans-2-(3-isopropyloxyphenyl)-1-hexanoyloxycyclohexane,
(1S, 2R)-trans-2-(4-isopropyloxyphenyl)-1-hexanoyloxycyclohexane,
(1S, 2R)-trans-2-(2-isopropyloxyphenyl)-1-hexanoyloxycyclohexane, (1S, 2R)-trans-2-(3-isopropyloxyphenyl)-1-hexanoyloxycyclohexane,
(1S, 2R)-trans-2-(4-isopropyloxyphenyl)-1-hexanoyloxycyclohexane,
(1S, 2R)-trans-2-(2-butoxyphenyl)-1-hexanoyloxycyclohexane,
(1S, 2R)-trans-2-(3-butoxyphenyl)-1-hexanoyloxycyclohexane,
(1S, 2R)-trans-2-(4-butoxyphenyl)-1-hexanoyloxycyclohexane,
(1S, 2R)-trans-2-(2-sec-butoxyphenyl)-1-hexanoyloxycyclohexane,
(1S, 2R)-trans-2-(3-sec-butoxyphenyl)-1-hexanoyloxycyclohexane,
(1S, 2R)-trans-2-(4-sec-butoxyphenyl)-1-hexanoyloxycyclohexane,
(1S, 2R)-trans-2-(2-tert-butoxyphenyl)-1-hexanoyloxycyclohexane,
(1S, 2R)-trans-2-(3-tert-butoxyphenyl)-1-hexanoyloxycyclohexane,
(1S, 2R)-trans-2-(4-tert-butoxyphenyl)-1-hexanoyloxycyclohexane,
(1S, 2R)-trans-2-(2-methoxymethyloxyphenyl)-1-hexanoyloxycyclohexane,
(1S, 2R)-trans-2-(3-methoxymethyloxyphenyl)-1-hexanoyloxycyclohexane,
(1S, 2R)-trans-2-(4-methoxymethyloxyphenyl)-1-hexanoyloxycyclohexane,
(1S, 2R)-trans-2-(2-methoxyethoxymethyloxyphenyl)-1-hexanoyloxycyclohexane,
(1S, 2R)-trans-2-(3-methoxyethoxymethyloxyphenyl)-1-hexanoyloxycyclohexane,
(1S, 2R)-trans-2-(4-methoxyethoxymethyloxyphenyl)-1-hexanoyloxycyclohexane,
(1S, 2R)-trans-2-(2-methylthiomethyloxyphenyl)-1-hexanoyloxycyclohexane,
(1S, 2R)-trans-2-(3-methylthiomethyloxyphenyl)-1-hexanoyloxycyclohexane,
(1S, 2R)-trans-2-(4-methylthiomethyloxyphenyl)-1-hexanoyloxycyclohexane,
(1S, 2R)-trans-2-(2-tetrahydropyranyloxyphenyl)-1-hexanoyloxycyclohexane,
(1S, 2R)-trans-2-(3-tetrahydropyranyloxyphenyl)-1-hexanoyloxycyclohexane,
(1S, 2R)-trans-2-(4-tetrahydropyranyloxyphenyl)-1-hexanoyloxycyclohexane,
(1S, 2R)-trans-2-(2-cyclopropylmethyloxyphenyl)-1-hexanoyloxycyclohexane,
(1S, 2R)-trans-2-(3-cyclopropylmethyloxyphenyl)-1-hexanoyloxycyclohexane,
(1S, 2R)-trans-2-(4-cyclopropylmethyloxyphenyl)-1-hexanoyloxycyclohexane,
(1S, 2R)-trans-2-(2-cyclohexyloxyphenyl)-1-hexanoyloxycyclohexane,
(1S, 2R)-trans-2-(3-cyclohexyloxyphenyl)-1-hexanoyloxycyclohexane,
(1S, 2R)-trans-2-(4-cyclohexyloxyphenyl)-1-hexanoyloxycyclohexane,
(1S, 2R)-trans-2-(2-allyloxyphenyl)-1-hexanoyloxycyclohexane,
(1S, 2R)-trans-2-(3-allyloxyphenyl)-1-hexanoyloxycyclohexane,
(1S, 2R)-trans-2-(4-allyloxyphenyl)-1-hexanoyloxycyclohexane,
(1S, 2R)-trans-2-(2-benzyloxyphenyl)-1-hexanoyloxycyclohexane,
(1S, 2R)-trans-2-(3-benzyloxyphenyl)-1-hexanoyloxycyclohexane,
(1S, 2R)-trans-2-(4-benzyloxyphenyl)-1-hexanoyloxycyclohexane,
(1S, 2R)-trans-2-(2-(9-anthrylmethyloxy)phenyl)-1-hexanoyloxycyclohexane,
(1S, 2R)-trans-2-(3-(9-anthrylmethyloxy)phenyl)-1-hexanoyloxycyclohexane,
(1S, 2R)-trans-2-(4-(9-anthrylmethyloxy)phenyl)-1-hexanoyloxycyclohexane,
(1S, 2R)-trans-2-(2-tert-butyldimethylsilyloxyphenyl)-1-hexanoyloxycyclohexane,
(1S, 2R)-trans-2-(3-tert-butyldimethylsilyloxyphenyl)-1-hexanoyloxycyclohexane,
(1S, 2R)-trans-2-(4-tert-butyldimethylsilyloxyphenyl)-1-hexanoyloxycyclohexane,
(1S, 2R)-trans-2-(2-methoxyphenyl)-1-dodecanoyloxycyclohexane,
(1S, 2R)-trans-2-(3-methoxyphenyl)-1-dodecanoyloxycyclohexane,
(1S, 2R)-trans-2-(4-methoxyphenyl)-1-dodecanoyloxycyclohexane,
(1S, 2R)-trans-2-(2-ethoxyphenyl)-1-dodecanoyloxycyclohexane,
(1S, 2R)-trans-2-(3-ethoxyphenyl)-1-dodecanoyloxycyclohexane,
(1S, 2R)-trans-2-(4-ethoxyphenyl)-1-dodecanoyloxycyclohexane,
(1S, 2R)-trans-2-(2-propyloxyphenyl)-1-dodecanoyloxycyclohexane,
(1S, 2R)-trans-2-(3-propyloxyphenyl)-1-dodecanoyloxycyclohexane,
(1S, 2R)-trans-2-(4-propyloxyphenyl)-1-dodecanoyloxycyclohexane,
(1S, 2R)-trans-2-(2-isopropyloxyphenyl)-1-dodecanoyloxycyclohexane,
(1S, 2R)-trans-2-(3-isopropyloxyphenyl)-1-dodecanoyloxycyclohexane,
(1S, 2R)-trans-2-(4-isopropyloxyphenyl)-1-dodecanoyloxycyclohexane,
(1S, 2R)-trans-2-(2-isopropyloxyphenyl)-1-dodecanoyloxycyclohexane,
(1S, 2R)-trans-2-(3-isopropyloxyphenyl)-1-dodecanoyloxycyclohexane,
(1S, 2R)-trans-2-(4-isopropyloxyphenyl)-1-dodecanoyloxycyclohexane,
(1S, 2R)-trans-2-(2-butoxyphenyl)-1-dodecanoyloxycyclohexane,
(1S, 2R -trans-2-(3-butoxyphenyl)-1-dodecanoyloxycyclohexane,
(1S, 2R)-trans-2-(4-butoxyphenyl)-1-dodecanoyloxycyclohexane,
(1S, 2R)-trans-2-(2-sec-butoxyphenyl)-1-dodecanoyloxycyclohexane,
(1S, 2R)-trans-2-(3-sec-butoxyphenyl)-1-dodecanoyloxycyclohexane,
(1S, 2R)-trans-2-(4-sec-butoxyphenyl)-1-dodecanoyloxycyclohexane,
(1S, 2R)-trans-2-(2-tert-butoxyphenyl)-1-dodecanoyloxycyclohexane,
(1S, 2R)-trans-2-(3-tert-butoxyphenyl)-1-dodecanoyloxycyclohexane,
(1S, 2R)-trans-2-(4-tert-butoxyphenyl)-1-dodecanoyloxycyclohexane,
(1S, 2R)-trans-2-(2-methoxymethyloxyphenyl)-1-dodecanoyloxycyclohexane,
(1S, 2R)-trans-2-(3-methoxymethyloxyphenyl)-1-dodecanoyloxycyclohexane,
(1S, 2R)-trans-2-(4-methoxymethyloxyphenyl)-1-dodecanoyloxycyclohexane, (1S, 2R)-trans-2-(2-methoxyethoxymethyloxyphenyl)-1-dodecanoyloxycyclohexane,
(1S, 2R)-trans-2-(3-methoxyethoxymethyloxyphenyl)-1-dodecanoyloxycyclohexane,
(1S, 2R)-trans-2-(4-methoxyethoxymethyloxyphenyl)-1-dodecanoyloxycyclohexane,
(1S, 2R)-trans-2-(2-methylthiomethyloxyphenyl)-1-dodecanoyloxycyclohexane,
(1S, 2R)-trans-2-(3-methylthiomethyloxyphenyl)-1-dodecanoyloxycyclohexane,
(1S, 2R)-trans-2-(4-methylthiomethyloxyphenyl)-1-dodecanoyloxycyclohexane,
(1S, 2R)-trans-2-(2-tetrahydropyranyloxyphenyl)-1-dodecanoyloxycyclohexane,
(1S, 2R)-trans-2-(3-tetrahydropyranyloxyphenyl)-1-dodecanoyloxycyclohexane,
(1S, 2R)-trans-2-(4-tetrahydropyranyloxyphenyl)-1-dodecanoyloxycyclohexane,
(1S, 2R)-trans-2-(2-cyclopropylmethyloxyphenyl)-1-dodecanoyloxycyclohexane,
(1S, 2R)-trans-2-(3-cyclopropylmethyloxyphenyl)-1-dodecanoyloxycyclohexane,
(1S, 2R)-trans-2-(4-cyclopropylmethyloxyphenyl)-1-dodecanoyloxycyclohexane,
(1S, 2R)-trans-2-(2-cyclohexyloxyphenyl)-1-dodecanoyloxycyclohexane,
(1S, 2R)-trans-2-(3-cyclohexyloxyphenyl)-1-dodecanoyloxycyclohexane,
(1S, 2R)-trans-2-(4-cyclohexyloxyphenyl)-1-dodecanoyloxycyclohexane,
(1S, 2R)-trans-2-(2-allyloxyphenyl)-1-dodecanoyloxycyclohexane,
(1S, 2R)-trans-2-(3-allyloxyphenyl)-1-dodecanoyloxycyclohexane,
(1S, 2R)-trans-2-(4-allyloxyphenyl)-1-dodecanoyloxycyclohexane,
(1S, 2R)-trans-2-(2-benzyloxyphenyl)-1-dodecanoyloxycyclohexane,
(1S, 2R)-trans-2-(3-benzyloxyphenyl)-1-dodecanoyloxycyclohexane,
(1S, 2R)-trans-2-(4-benzyloxyphenyl)-1-dodecanoyloxycyclohexane,
(1S, 2R)-trans-2-(2-(9-anthrylmethyloxy)phenyl)-1-dodecanoyloxycyclohexane,
(1S, 2R)-trans-2-(3-(9-anthrylmethyloxy)phenyl)-1-dodecanoyloxycyclohexane,
(1S, 2R)-trans-2-(4-(9-anthrylmethyloxy)phenyl)-1-dodecanoyloxycyclohexane,
(1S, 2R)-trans-2-(2-tert-butyldimethylsilyloxyphenyl)-1-dodecanoyloxycyclohexane,
(1S, 2R)-trans-2-(3-tert-butyldimethylsilyloxyphenyl)-1-dodecanoyloxycyclohexane,
(1S, 2R)-trans-2-(4-tert-butyldimethylsilyloxyphenyl)-1-dodecanoyloxycyclohexane,
(1R, 2S)-trans-2-(2-hydroxyphenyl)-1-cyclohexanol,
(1R, 2S)-trans-2-(3-hydroxyphenyl)-1-cyclohexanol,
(1R, 2S)-trans-2-(4-hydroxyphenyl)-1-cyclohexanol,
(1R, 2S)-trans-2-(2-methoxyphenyl)-1-cyclohexanol,
(1R, 2S)-trans-2-(3-methoxyphenyl)-1-cyclohexanol,
(1R, 2S)-trans-2-(4-methoxyphenyl)-1-cyclohexanol,
(1R, 2S)-trans-2-(2-ethoxyphenyl)-1-cyclohexanol,
(1R, 2S)-trans-2-(3-ethoxyphenyl)-1-cyclohexanol,
(1R, 2S)-trans-2-(4-ethoxyphenyl)-1-cyclohexanol,
(1R, 2S)-trans-2-(2-propyloxyphenyl)-1-cyclohexanol,
(1R, 2S)-trans-2-(3-propyloxyphenyl)-1-cyclohexanol,
(1R, 2S)-trans-2-(4-propyloxyphenyl)-1-cyclohexanol,
(1R, 2S)-trans-2-(2-isopropyloxyphenyl)-1-cyclohexanol,
(1R, 2S)-trans-2-(3-isopropyloxyphenyl)-1-cyclohexanol,
(1R, 2S)-trans-2-(4-isopropyloxyphenyl)-1-cyclohexanol,
(1R, 2S)-trans-2-(2-butoxyphenyl)-1-cyclohexanol,
(1R, 2S)-trans-2-(3-butoxyphenyl)-1-cyclohexanol,
(1R, 2S)-trans-2-(4-butoxyphenyl)-1-cyclohexanol,
(1R, 2S)-trans-2-(2-sec-butoxyphenyl)-1-cyclohexanol,
(1R, 2S)-trans-2-(3-sec-butoxyphenyl)-1-cyclohexanol,
(1R, 2S)-trans-2-(4-sec-butoxyphenyl)-1-cyclohexanol,
(1R, 2S)-trans-2-(2-tert-butoxyphenyl)-1-cyclohexanol,
(1R, 2S)-trans-2-(3-tert-butoxyphenyl)-1-cyclohexanol,
(1R, 2S)-trans-2-(4-tert-butoxyphenyl)-1-cyclohexanol,
(1R, 2S)-trans-2-(2-methoxymethyloxyphenyl)-1-cyclohexanol,
(1R, 2S)-trans-2-(3-methoxymethyloxyphenyl)-1-cyclohexanol,
(1R, 2S)-trans-2-(4-methoxymethyloxyphenyl)-1-cyclohexanol,
(1R, 2S)-trans-2-(2-methoxyethoxymethyloxyphenyl)-1-cyclohexanol,
(1R, 2S)-trans-2-(3-methoxyethoxymethyloxyphenyl)-1-cyclohexanol,
(1R, 2S)-trans-2-(4-methoxyethoxymethyloxyphenyl)-1-cyclohexanol,
(1R, 2S)-trans-2-(2-methylthiomethyloxyphenyl)-1-cyclohexanol,
(1R, 2S)-trans-2-(3-methylthiomethyloxyphenyl)-1-cyclohexanol,
(1R, 2S)-trans-2-(4-methylthiomethyloxyphenyl)-1-cyclohexanol,
(1R, 2S)-trans-2-(2-tetrahydropyranyloxyphenyl)-1-cyclohexanol,
(1R, 2S)-trans-2-(3-tetrahydropyranyloxyphenyl)-1-cyclohexanol,
(1R, 2S)-trans-2-(4-tetrahydropyranyloxyphenyl)-1-cyclohexanol,
(1R, 2S)-trans-2-(2-cyclopropylmethyloxyphenyl)-1-cyclohexanol,
(1R, 2S)-trans-2-(3-cyclopropylmethyloxyphenyl)-1-cyclohexanol,
(1R, 2S)-trans-2-(4-cyclopropylmethyloxyphenyl)-1-cyclohexanol,
(1R, 2S)-trans-2-(2-cyclohexyloxyphenyl)-1-cyclohexanol,
(1R, 2S)-trans-2-(3-cyclohexyloxyphenyl)-1-cyclohexanol,
(1R, 2S)-trans-2-(4-cyclohexyloxyphenyl)-1-cyclohexanol,
(1R, 2S)-trans-2-(2-allyloxyphenyl)-1-cyclohexanol,
(1R, 2S)-trans-2-(3-allyloxyphenyl)-1-cyclohexanol,
(1R, 2S)-trans-2-(4-allyloxyphenyl)-1-cyclohexanol,
(1R, 2S)-trans-2-(2-benzyloxyphenyl)-1-cyclohexanol,
(1R, 2S)-trans-2-(3-benzyloxyphenyl)-1-cyclohexanol,
(1R, 2S)-trans-2-(4-benzyloxyphenyl)-1-cyclohexanol, (1R, 2S)-trans-2-(2-(9-anthrylmethyloxy)phenyl)-1-cyclohexanol,
(1R, 2S)-trans-2-(3-(9-anthrylmethyloxy)phenyl)-1-cyclohexanol,
(1R, 2S)-trans-2-(4-(9-anthrylmethyloxy)phenyl)-1-cyclohexanol,
(1R, 2S)-trans-2-(2-tert-butyldimethylsilyloxyphenyl)-1-cyclohexanol,
(1R, 2S)-trans-2-(3-tert-butyldimethylsilyloxyphenyl)-1-cyclohexanol,
(1R, 2S)-trans-2-(4-tert-butyldimethylsilyloxyphenyl)-1-cyclohexanol,
(1R, 2S)-trans-2-(2-methoxyphenyl)-1-acetyloxycyclohexane,
(1R, 2S)-trans-2-(3-methoxyphenyl)-1-acetyloxycyclohexane,
(1R, 2S)-trans-2-(4-methoxyphenyl)-1-acetyloxycyclohexane,
(1R, 2S)-trans-2-(2-ethoxyphenyl)-1-acetyloxycyclohexane,
(1R, 2S)-trans-2-(3-ethoxyphenyl)-1-acetyloxycyclohexane,
(1R, 2S)-trans-2-(4-ethoxyphenyl)-1-acetyloxycyclohexane,
(1R, 2S)-trans-2-(2-propyloxyphenyl)-1-acetyloxycyclohexane,
(1R, 2S)-trans-2-(3-propyloxyphenyl)-1-acetyloxycyclohexane,
(1R, 2S)-trans-2-(4-propyloxyphenyl)-1-acetyloxycyclohexane,
(1R, 2S)-trans-2-(2-isopropyloxyphenyl)-1-acetyloxycyclohexane,
(1R, 2S)-trans-2-(3-isopropyloxyphenyl)-1-acetyloxycyclohexane,
(1R, 2S)-trans-2-(4-isopropyloxyphenyl)-1-acetyloxycyclohexane,
(1R, 2S)-trans-2-(2-isopropyloxyphenyl)-1-acetyloxycyclohexane,
(1R, 2S -trans-2-(3-isopropyloxyphenyl)-1-acetyloxycyclohexane,
(1R, 2R -trans-2-(4-isopropyloxyphenyl)-1-acetyloxycyclohexane,
(1R, 2S -trans-2-(2-butoxyphenyl)-1-acetyloxycyclohexane,
(1R, 2S)-trans-2-(3-butoxyphenyl)-1-acetyloxycyclohexane,
(1R, 2S)-trans-2-(4-butoxyphenyl)-1-acetyloxycyclohexane,
(1R, 2S)-trans-2-(2-sec-butoxyphenyl)-1-acetyloxycyclohexane,
(1R, 2S)-trans-2-(3-sec-butoxyphenyl)-1-acetyloxycyclohexane,
(1R, 2S)-trans-2-(4-sec-butoxyphenyl)-1-acetyloxycyclohexane,
(1R, 2S)-trans-2-(2-tert-butoxyphenyl)-1-acetyloxycyclohexane,
(1R, 2S)-trans-2-(3-tert-butoxyphenyl)-1-acetyloxycyclohexane,
(1R, 2S)-trans-2-(4-tert-butoxyphenyl)-1-acetyloxycyclohexane,
(1R, 2S)-trans-2-(2-methoxymethyloxyphenyl)-1-acetyloxycyclohexane,
(1R, 2S)-trans-2-(3-methoxymethyloxyphenyl)-1-acetyloxycyclohexane,
(1R, 2S)-trans-2-(4-methoxymethyloxyphenyl)-1-acetyloxycyclohexane,
(1R, 2S)-trans-2-(2-methoxyethoxymethyloxyphenyl)-1-acetyloxycyclohexane,
(1R, 2S)-trans-2-(3-methoxyethoxymethyloxyphenyl)-1-acetyloxycyclohexane,
(1R, 2S)-trans-2-(4-methoxyethoxymethyloxyphenyl)-1-acetyloxycyclohexane,
(1R, 2S)-trans-2-(2-methylthiomethyloxyphenyl)-1-acetyloxycyclohexane,
(1R, 2S)-trans-2-(3-methylthiomethyloxyphenyl)-1-acetyloxycyclohexane,
(1R, 2S)-trans-2-(4-methylthiomethyloxyphenyl)-1-acetyloxycyclohexane,
(1R, 2S)-trans-2-(2-tetrahydropyranyloxyphenyl)-1-acetyloxycyclohexane,
(1R, 2S)-trans-2-(3-tetrahydropyranyloxyphenyl)-1-acetyloxycyclohexane,
(1R, 2S)-trans-2-(4-tetrahydropyranyloxyphenyl)-1-acetyloxycyclohexane,
(1R, 2S)-trans-2-(2-cyclopropylmethyloxyphenyl)-1-acetyloxycyclohexane,
(1R, 2S)-trans-2-(3-cyclopropylmethyloxyphenyl)-1-acetyloxycyclohexane,
(1R, 2S)-trans-2-(4-cyclopropylmethyloxyphenyl)-1-acetyloxycyclohexane,
(1R, 2S)-trans-2-(2-cyclohexyloxyphenyl)-1-acetyloxycyclohexane,
(1R, 2S)-trans-2-(3-cyclohexyloxyphenyl)-1-acetyloxycyclohexane,
(1R, 2S)-trans-2-(4-cyclohexyloxyphenyl)-1-acetyloxycyclohexane,
(1R, 2S)-trans-2-(2-allyloxyphenyl)-1-acetyloxycyclohexane,
(1R, 2S)-trans-2-(3-allyloxyphenyl)-1-acetyloxycyclohexane,
(1R, 2S)-trans-2-(4-allyloxyphenyl)-1-acetyloxycyclohexane,
(1R, 2S)-trans-2-(2-benzyloxyphenyl)-1-acetyloxycyclohexane,
(1R, 2S)-trans-2-(3-benzyloxyphenyl)-1-acetyloxycyclohexane,
(1R, 2S)-trans-2-(4-benzyloxyphenyl)-1-acetyloxycyclohexane,
(1R, 2S)-trans-2-(2-(9-anthrylmethyloxy)phenyl)-1-acetyloxycyclohexane,
(1R, 2S)-trans-2-(3-(9-anthrylmethyloxy)phenyl)-1-acetyloxycyclohexane,
(1R, 2S)-trans-2-(4-(9-anthrylmethyloxy)phenyl)-1-acetyloxycyclohexane,
(1R, 2S)-trans-2-(2-tert-butyldimethylsilyloxyphenyl)-1-acetyloxycyclohexane,
(1R, 2S)-trans-2-(3-tert-butyldimethylsilyloxyphenyl)-1-acetyloxycyclohexane,
(1R, 2S)-trans-2-(4-tert-butyldimethylsilyloxyphenyl)-1-acetyloxycyclohexane,
(1R, 2S)-trans-2-(2-methoxyphenyl)-1-propanoyloxycyclohexane,
(1R, 2S)-trans-2-(3-methoxyphenyl)-1-propanoyloxycyclohexane,
(1R, 2S)-trans-2-(4-methoxyphenyl)-1-propanoyloxycyclohexane,
(1R, 2S)-trans-2-(2-ethoxyphenyl)-1-propanoyloxycyclohexane,
(1R, 2S)-trans-2-(3-ethoxyphenyl)-1-propanoyloxycyclohexane,
(1R, 2S)-trans-2-(4 -ethoxyphenyl)-1-propanoyloxycyclohexane,
(1R, 2S)-trans-2-(2-propyloxyphenyl)-1-propanoyloxycyclohexane,
(1R, 2S)-trans-2-(3-propyloxyphenyl)-1-propanoyloxycyclohexane, (1R, 2S)-trans-2-(4-propyloxyphenyl)-1-propanoyloxycyclohexane,
(1R, 2S)-trans-2-(2-isopropyloxyphenyl)-1-propanoyloxycyclohexane,
(1R, 2S)-trans-2-(3-isopropyloxyphenyl)-1-propanoyloxycyclohexane,
(1R, 2S)-trans-2-(4-isopropyloxyphenyl)-1-propanoyloxycyclohexane,
(1R, 2S)-trans-2-(2-isopropyloxyphenyl)-1-propanoyloxycyclohexane,
(1R, 2S)-trans-2-(3-isopropyloxyphenyl)-1-propanoyloxycyclohexane,
(1R, 2S)-trans-2-(4-isopropyloxyphenyl)-1-propanoyloxycyclohexane,
(1R, 2S)-trans-2-(2-butoxyphenyl)-1-propanoyloxycyclohexane,
(1R, 2S)-trans-2-(3-butoxyphenyl)-1-propanoy loxycyclohexane,
(1R, 2S)-trans-2-(4-butoxyphenyl)-1-propanoy loxycyclohexane,
(1R, 2S)-trans-2-(2-sec-butoxyphenyl)-1-propanoy loxycyclohexane,
(1R, 2S)-trans-2-(3-sec-butoxyphenyl)-1-propanoyloxycyclohexane,
(1R, 2S)-trans-2-(4-sec-butoxyphenyl)-1-propanoy loxycyclohexane,
(1R, 2S)-trans-2-(2-tert-butoxyphenyl)-1-propanoyloxycyclohexane,
(1R, 2S)-trans-2-(3-tert-butoxyphenyl)-1-propanoyloxycyclohexane,
(1R, 2S)-trans-2-(4-tert-butoxyphenyl)-1-propanoyloxycyclohexane,
(1R, 2S)-trans-2-(2-methoxymethyloxyphenyl)-1-propanoyloxycyclohexane,
(1R, 2S)-trans-2-(3-methoxymethyloxyphenyl)-1-propanoyloxycyclohexane,
(1R, 2S)-trans-2-(4-methoxymethyloxyphenyl)-1-propanoyloxycyclohexane,
(1R, 2S)-trans-2-(2-methoxyethoxymethyloxyphenyl)-1-propanoyloxycyclohexane,
(1R, 2S)-trans-2-(3-methoxyethoxymethyloxyphenyl)-1-propanoyloxycyclohexane,
(1R, 2S)-trans-2-(4-methoxyethoxymethyloxyphenyl)-1-propanoyloxycyclohexane,
(1R, 2S)-trans-2-(2-methylthiomethyloxyphenyl)-1-propanoyloxycyclohexane,
(1R, 2S)-trans-2-(3-methylthiomethyloxyphenyl)-1-propanoyloxycyclohexane,
(1R, 2S)-trans-2-(4-methylthiomethyloxyphenyl)-1-propanoyloxycyclohexane,
(1R, 2S)-trans-2-(2-tetrahydropyranyloxyphenyl)-1-propanoyloxycyclohexane,
(1R, 2S)-trans-2-(3-tetrahydropyranyloxyphenyl)-1-propanoyloxycyclohexane,
(1R, 2S)-trans-2-(4-tetrahydropyranyloxyphenyl)-1-propanoyloxycyclohexane,
(1R, 2S)-trans-2-(2-cyclopropylmethyloxyphenyl)-1-propanoyloxycyclohexane,
(1R, 2S)-trans-2-(3-cyclopropylmethyloxyphenyl)-1-propanoyloxycyclohexane,
(1R, 2S)-trans-2-(4-cyclopropylmethyloxyphenyl)-1-propanoyloxycyclohexane,
(1R, 2S)-trans-2-(2-cyclohexyloxyphenyl)-1-propanoyloxycyclohexane,
(1R, 2S)-trans-2-(3-cyclohexyloxyphenyl)-1-propanoyloxycyclohexane,
(1R, 2S)-trans-2-(4-cyclohexyloxyphenyl)-1-propanoyloxycyclohexane,
(1R, 2S)-trans-2-(2-allyloxyphenyl)-1-propanoyloxycyclohexane,
(1R, 2S)-trans-2-(3-allyloxyphenyl)-1-propanoyloxycyclohexane,
(1R, 2S)-trans-2-(4-allyloxyphenyl)-1-propanoy loxycyclohexane,
(1R, 2S)-trans-2-(2-benzyloxyphenyl)-1-propanoyloxycyclohexane,
(1R, 2S)-trans-2-(3-benzyloxyphenyl)-1-propanoyloxycyclohexane,
(1R, 2S)-trans-2-(4-benzyloxyphenyl)-1-propanoy loxycyclohexane,
(1R, 2S)-trans-2-(2-(9-anthrylmethyloxy)phenyl)-1-propanoyloxycyclohexane,
(1R, 2S)-trans-2-(3-(9-anthrylmethyloxy)phenyl)-1-propanoyloxycyclohexane,
(1R, 2S)-trans-2-(4-(9-anthrylmethyloxy)phenyl)-1-propanoyloxycyclohexane,
(1R, 2S)-trans-2-(2-tert-butyldimethylsilyloxyphenyl)-1-propanoyloxycyclohexane,
(1R, 2S)-trans-2-(3-tert-butyldimethylsilyloxyphenyl)-1-propanoyloxycyclohexane,
(1R, 2S)-trans-2-(4-tert-butyldimethylsilyloxyphenyl)-1-propanoyloxycyclohexane,
(1R, 2S)-trans-2-(2-methoxyphenyl)-1-hexanoyloxycyclohexane,
(1R, 2S)-trans-2-(3-methoxyphenyl)-1-hexanoyloxycyclohexane,
(1R, 2)-trans-2-(4-methoxyphenyl)-1-hexanoyloxycyclohexane,
(1R, 2S)-trans-2-(2-ethoxyphenyl)-1-hexanoyloxycyclohexane,
(1R, 2S)-trans-2-(3-ethoxyphenyl)-1-hexanoyloxycyclohexane,
(1R, 2S)-trans-2-(4-ethoxyphenyl)-1-hexanoyloxycyclohexane,
(1R, 2S)-trans-2-(2-propyloxyphenyl)-1-hexanoyloxycyclohexane,
(1R, 2S)-trans-2-(3-propyloxyphenyl)-1-hexanoyloxycyclohexane,
(1R, 2S)-trans-2-(4-propyloxyphenyl)-1-hexanoyloxycyclohexane,
(1R, 2S)-trans-2-(2-isopropyloxyphenyl)-1-hexanoyloxycyclohexane,
(1R, 2S)-trans-2-(3-isopropyloxyphenyl)-1-hexanoyloxycyclohexane,
(1R, 2S)-trans-2-(4-isopropyloxyphenyl)-1-hexanoyloxycyclohexane,
(1R, 2S)-trans-2-(2-isopropyloxyphenyl)-1-hexanoyloxycyclohexane,
(1R, 2S)-trans-2-(3-isopropyloxyphenyl)-1-hexanoyloxycyclohexane,
(1R, 2S)-trans-2-(4-isopropyloxyphenyl)-1-hexanoyloxycyclohexane,
(1R, 2S)-trans-2-(2-butoxyphenyl)-1-hexanoyloxycyclohexane,
(1R, 2S)-trans-2-(3-butoxyphenyl)-1-hexanoyloxycyclohexane,
(1R, 2S)-trans-2-(4-butoxyphenyl)-1-hexanoyloxycyclohexane,
(1R, 2S)-trans-2-(2-sec-butoxyphenyl)-1-hexanoy loxycyclohexane,
(1R, 2S)-trans-2-(3-sec-butoxyphenyl)-1-hexanoyloxycyclohexane,
(1R, 2S)-trans-2-(4-sec-butoxyphenyl)-1-hexanoyloxycyclohexane,
(1R, 2S)-trans-2-(2-tert-butoxyphenyl)-1-hexanoy loxycyclohexane, (1R, 2S)-trans-2-(3-tert-butoxyphenyl)-1-hexanoyloxycyclohexane,
(1R, 2S)-trans-2-(4-tert-butoxyphenyl)-1-hexanoyloxycyclohexane,
(1R, 2S)-trans-2-(2-methoxymethyloxyphenyl)-1-hexanoyloxycyclohexane,
(1R, 2S)-trans-2-(3-methoxymethyloxyphenyl)-1-hexanoyloxycyclohexane,
(1R, 2S)-trans-2-(4-methoxymethyloxyphenyl)-1-hexanoyloxycyclohexane,
(1R, 2S)-trans-2-(2-methoxyethoxymethyloxyphenyl)-1-hexanoyloxycyclohexane,
(1R, 2S)-trans-2-(3-methoxyethoxymethyloxyphenyl)-1-hexanoyloxycyclohexane,
(1R, 2S)-trans-2-(4-methoxyethoxymethyloxyphenyl)-1-hexanoyloxycyclohexane,
(1R, 2S)-trans-2-(2-methylthiomethyloxyphenyl)-1-hexanoyloxycyclohexane,
(1R, 2S)-trans-2-(3-methylthiomethyloxyphenyl)-1-hexanoyloxycyclohexane,
(1R, 2S)-trans-2-(4-methylthiomethyloxyphenyl)-1-hexanoyloxycyclohexane,
(1R, 2S)-trans-2-(2-tetrahydropyranyloxyphenyl)-1-hexanoyloxycyclohexane,
(1R, 2S)-trans-2-(3-tetrahydropyranyloxyphenyl)-1-hexanoyloxycyclohexane,
(1R, 2S)-trans-2-(4-tetrahydropyranyloxyphenyl)-1-hexanoyloxycyclohexane,
(1R, 2S)-trans-2-(2-cyclopropylmethyloxyphenyl)-1-hexanoyloxycyclohexane,
(1R, 2S)-trans-2-(3-cyclopropylmethyloxyphenyl)-1-hexanoyloxycyclohexane,
(1R, 2S)-trans-2-(4-cyclopropylmethyloxyphenyl)-1-hexanoyloxycyclohexane,
(1R, 2S)-trans-2-(2-cyclohexyloxyphenyl)-1-hexanoyloxycyclohexane,
(1R, 2S)-trans-2-(3-cyclohexyloxyphenyl)-1-hexanoyloxycyclohexane,
(1R, 2S)-trans-2-(4-cyclohexyloxyphenyl)-1-hexanoyloxycyclohexane,
(1R, 2S)-trans-2-(2-allyloxyphenyl)-1-hexanoyloxycyclohexane,
(1R, 2S)-trans-2-(3-allyloxyphenyl)-1-hexanoyloxycyclohexane,
(1R, 2S)-trans-2-(4-allyloxyphenyl)-1-hexanoyloxycyclohexane,
(1R, 2S)-trans-2-(2-benzyloxyphenyl)-1-hexanoyloxycyclohexane,
(1R, 2S)-trans-2-(3-benzyloxyphenyl)-1-hexanoyloxycyclohexane,
(1R, 2S)-trans-2-(4-benzyloxyphenyl)-1-hexanoyloxycyohexane,
(1R, 2S)-trans-2-(2-(9-anthrylmethyloxy)phenyl)-1-hexanoyloxycyclohexane,
(1R, 2S)-trans-2-(3-(9-anthrylmethyloxy)phenyl)-1-hexanoyloxycyclohexane,
(1R, 2S)-trans-2-(4-(9-anthrylmethyloxy)phenyl)-1-hexanoyloxycyclohexane,
(1R, 2S)-trans-2-(2-tert-butyldimethylsilyloxyphenyl)-1-hexanoyloxycyclohexane,
(1R, 2S)-trans-2-(3-tert-butyldimethylsilyloxyphenyl)-1-hexanoyloxycyclohexane,
(1R, 2S)-trans-2-(4-tert-butyldimethylsilyloxyphenyl)-1-hexanoyloxycyclohexane,
(1R, 2S)-trans-2-(2-methoxyphenyl)-1-dodecanoyloxycyclohexane,
(1R, 2S)-trans-2-(3-methoxyphenyl)-1-dodecanoyloxycyclohexane,
(1R, 2S)-trans-2-(4-methoxyphenyl-1-dodecanoyloxycyclohexane,
(1R, 2S)-trans-2-(2-ethoxyphenyl)1-dodecanoyloxycyclohexane,
(1R, 2S)-trans-2-(3-ethoxyphenyl)1-dodecanoyloxycyclohexane,
(1R, 2S)-trans-2-(4-ethoxyphenyl)1-dodecanoyloxycyclohexane,
(1R, 2S)-trans-2-(2-propyloxyphenyl)-1-dodecanoyloxycyclohexane,
(1R, 2S)-trans-2-(3-propyloxyphenyl)-1-dodecanoyloxycyclohexane,
(1R, 2S)-trans-2-(4-propyloxyphenyl)-1-dodecanoyloxycyclohexane,
(1R, 2S)-trans-2-(2-isopropyloxyphenyl)-1-dodecanoyloxycyclohexane,
(1R, 2S)-trans-2-(3-isopropyloxyphenyl)-1-dodecanoyloxycyclohexane,
(1R, 2S)-trans-2-(4-isopropyloxyphenyl)-1-dodecanoyloxycyclohexane,
(1R, 2S)-trans-2-(2-isopropyloxyphenyl)-1-dodecanoyloxycyclohexane,
(1R, 2S)-trans-2-(3-isopropyloxyphenyl)-1-dodecanoyloxycyclohexane,
(1R, 2S)-trans-2-(4-isopropyloxyphenyl)-1-dodecanoyloxycyclohexane,
(1R, 2S)-trans-2-(2-butoxyphenyl)-1-dodecanoyloxycyclohexane,
(1R, 2S)-trans-2-(3-butoxyphenyl)-1-dodecanoyloxycyclohexane,
(1R, 2S)-trans-2-(4-butoxyphenyl)-1-dodecanoyloxycyclohexane,
(1R, 2S)-trans-2-(2-sec-butoxyphenyl)-1-dodecanoyloxycyclohexane,
(1R, 2S)-trans-2-(3-sec-butoxyphenyl)-1-dodecanoyloxycyclohexane,
(1R, 2S)-trans-2-(4-sec-butoxyphenyl)-1-dodecanoyloxycyclohexane,
(1R, 2S)-trans-2-(2-tert-butoxyphenyl)-1-dodecanoyloxycyclohexane,
(1R, 2S)-trans-2-(3-tert-butoxyphenyl)-1-dodecanoyloxycyclohexane,
(1R, 2S)-trans-2-(4-tert-butoxyphenyl)-1-dodecanoyloxycyclohexane,
(1R, 2S)-trans-2-(2-methoxymethyloxyphenyl)-1-dodecanoyloxycyclohexane,
(1R, 2S)-trans-2-(3-methoxymethyloxyphenyl)-1-dodecanoyloxycyclohexane,
(1R, 2S)-trans-2-(4-methoxymethyloxyphenyl)-1-dodecanoyloxycyclohexane,
(1R, 2S)-trans-2-(2-methoxyethoxymethyloxyphenyl)-1-dodecanoyloxycyclohexane,
(1R, 2S)-trans-2-(3-methoxyethoxymethyloxyphenyl)-1-dodecanoyloxycyclohexane,
(1R, 2S)-trans-2-(4-methoxyethoxymethyloxyphenyl)-1-dodecanoyloxycyclohexane,
(1R, 2S)-trans-2-(2-methylthiomethyloxyphenyl)-1-dodecanoyloxycyclohexane,
(1R, 2S)-trans-2-(3-methylthiomethyloxyphenyl)-1-dodecanoyloxycyclohexane,
(1R, 2S)-trans-2-(4-methylthiomethyloxyphenyl)-1-dodecanoyloxycyclohexane,
(1R, 2S)-trans-2-(2-tetrahydropyranyloxyphenyl)-1-dodecanoyloxycyclohexane,
(1R, 2S)-trans-2-(3-tetrahydropyranyloxyphenyl)-1-dodecanoyloxycyclohexane,
(1R, 2S)-trans-2-(4-tetrahydropyranyloxyphenyl)-1-dodecanoyloxycyclohexane, (1R, 2S)-trans-2-(2-cyclopropylmethyloxyphenyl)-1-dodecanoyloxycyclohexane, (1R, 2S)-trans-2-(3-cyclopropylmethyloxyphenyl)-1-dodecanoyloxycyclohexane, (1R, 2S)-trans-2-(4-cyclopropylmethyloxyphenyl)-1-dodecanoyloxycyclohexane, (1R, 2S)-trans-2-(2-cyclohexyloxyphenyl)-1-dodecanoyloxycyclohexane, (1R, 2S)-trans-2-(3-cyclohexyloxyphenyl)-1-dodecanoyloxycyclohexane, (1R, 2S)-trans-2-(4-cyclohexyloxyphenyl)-1-dodecanoyloxycyclohexane, (1R, 2S)-trans-2-(2-allyloxyphenyl)-1-dodecanoyloxycyclohexane, (1R, 2S)-trans-2-(3-allyloxyphenyl)-1-dodecanoyloxycyclohexane, (1R, 2S)-trans-2-(4-allyloxyphenyl)-1-dodecanoyloxycyclohexane, (1R, 2S)-trans-2-(2-benzyloxyphenyl)-1-dodecanoyloxycyclohexane, (1R, 2S)-trans-2-(3-benzyloxyphenyl)-1-dodecanoyloxycyclohexane, (1R, 2S)-trans-2-(4-benzyloxyphenyl)-1-dodecanoyloxycyclohexane, (1R, 2S)-trans-2-(2-(9-anthrylmethyloxy)phenyl)-1-dodecanoyloxycyclohexane, (1R, 2S)-trans-2-(3-(9-anthrylmethyloxy)phenyl)-1-dodecanoyloxycyclohexane, (1R, 2S)-trans-2-(4-(9-anthrylmethyloxy)phenyl)-1-dodecanoyloxycyclohexane, (1R, 2S)-trans-2-(2-tert-butyldimethylsilyloxyphenyl)-1-dodecanoyloxycyclohexane, (1R, 2S)-trans-2-(3-tert-butyldimethylsilyloxyphenyl)-1-dodecanoyloxycyclohexane, and (1R, 2S)-trans-2-(4-tert-butyldimethylsilyloxyphenyl)-1-dodecanoyloxycyclohexane.

The process of the present invention, namely, the process for producing optically active trans-2-allyl-1-cyclohexanol derivatives comprises mixing (±)-trans-2-allyl-1-cyclohexanol with 0.5 equivalent of an acylating agent, namely a fatty acid vinyl ester or a triglyceride and efficiently contacting the mixture with esterase. The reaction temperature is suitably 10° C. to 150° C., especially preferably 20° C. to 45° C. The reaction time which depends on the acylating agent is 1to 1000 hours. The equivalent ratio of (±)-trans-2-aryl-1-cyclohexanol and the fatty acid vinyl ester or the triglyceride is 1:0.01 to large excess, preferably 0.5.

As described above, after the transesterification is conducted, the esterase can be removed by a common filter and can be reused as it is. Optically active trans-2-aryl-1-cyclohexanols and optically active trans-2-aryl-1-acyloxycyclohexanes can be obtained by distillation under reduced pressure, recrystallization or column chromatography of the filtrate of the reaction liquid. After the reaction was finished, if the optical purities of the residue of trans-2-aryl-1-cyclohexanol which is not acylated are low, namely, if the transesterification reaction is insufficiently conducted, the transesterification reaction is done again to obtain compounds having high optical purities.

In addition, either (+) or (−) of obtained optically active trans-2-aryl-1-cyclohexanol derivatives depend on the esterase.

(±)-Trans-2-aryl-1-cyclohexanols which are starting materials in the production method of the present invention can easily be synthesized by a method reported by Hyun et al. (Tetrahedron Lett., 1979, 1503).

Namely, a bromophenol derivative in which a hydroxy group was previously protected by a conventional method is transformed into a Grignard reagent, cyclohexene oxide is reacted with the Grignard reagent in the presence of cuprous chloride, and the (+)-trans-2-aryl-1-cyclohexanol can easily be obtained.

As the fatty acid vinyl ester which is used in the present invention, vinyl acetate, vinyl propionate, vinyl caproate, vinyl laurate, etc. can be exemplified. As the triglyceride which is used in the present invention, triacetin, tripropionin, tricaproin, trilaurin, etc. can be exemplified. These compounds are easily available.

As the esterase usable in the present invention, the esterase produced by microorganisms or originated from animals can be exemplified. The following table shows commercially available esterases.

TABLE

| Trade name | Origin | Seller or Maker |
|---|---|---|
| Lipase PS | Pseudomonas fluorescens | Amano Pharmaceutical Co., Ltd |
| Lipase CES | Pseudomonas sp | Amano Pharmaceutical Co., Ltd |
| Lipase AP | Aspergillus niger | Amano Pharmaceutical Co., Ltd |
| Lipase M | Mucor javanicus | Amano Pharmaceutical Co., Ltd |
| Lipase CE | Humicola lanuginosa | Amano Pharmaceutical Co., Ltd |
| Lipase F-AP | Rhizopus javanicus | Amano Pharmaceutical Co., Ltd |
| Lipase II | Porcine pancreas | Sigma Chemical Co., Ltd |
| Lipase VIII | Geotrichum candidum | Sigma Chemical Co., Ltd |
| Lipase X | Rhizopus delamar | Sigma Chemical Co., Ltd |
| Lipase | Chromobacterium viscosum | Toyo Jozo Co., Ltd |
| Lipase A | Aspergillus niger | Novo Industi A/S |
| Lipase | Rhizopus niveus | Nagase Biochemicals, Co. Ltd |
| Lipase B | Pseudomonas flaji | Sapporo Beer Co., Ltd |

In addition to these esterases, microorganisms which produce the esterases having the above ability can be used regardless of their species and genus. As such microorganisms, the genera Pseudomonas,
Arthrobacter,
Acromobacter,
Alcaligenes,
Asperigillus,
Chromobacterium,
Candida,
Mucor,
Rhizopus, etc, can be exemplified.

Particularly preferable esterase originates from Pseudomonas.

These esterases are used in powder or in granules. As a reaction solvent, a hydrocarbon type solvent such as n-hexane or n-heptane, benzene, toluene, ethers or ethyl acetate can be used. Any solvent which does not inhibit the esterase activity can widely be used.

Further, when the (±)-trans-2-aryl-1-cyclohexanol used is easily dissolved in fatty acid vinyl esters or triglycerides, the compound can be made to react without such a solvent.

Optically active trans-2-aryl-1-acyloxycyclohexane obtainable in the production process of the present invention can be hydrolyzed in an alkali solution (potassium hydroxide, sodium hydroxide, potassium carbonate, etc. can be used as a base)or in an acid solution (hydrochloric acid, sulfuric acid, etc. can be used as an acid), decomposed in an alcohol solution (such as methanol or ethanol), reduced (by using lithium aluminum hydride as a reducing agent)or the like to derive optically active trans-2-aryl-1-cyclohexanols. Obtained compounds are enantiomers of optically active trans-2-aryl-1-cyclohexanols, namely the residues which are obtained by the transesterification reaction of the present invention.

By the above described process, the optically active (+)—or (−)-trans-2-aryl-1-cyclohexanols and their derivatives can be obtained, respectively.

DESCRIPTION OF PREFERRED EMBODIMENTS

The following examples illustrate the present invention more specifically, but these will not always be precise in practical applications.

EXAMPLE 1

I) Synthesis of o-methoxyphenylbromide

Into a three-necked flask of 1liter, 25g (0.145 mol) of o-bromophenol, 6.1 g (0,152mol) of sodium hydroxide and 300 ml of ethanol were charged and refluxed for two hours. Then, 82.0 g (0.578 mol) of methyl iodide was added dropwise and the mixture was refluxed further for four hours. After the mixture was cooled to room temperature, 600 ml of diethyl ether was added. The mixture was charged into a separatory funnel. Separated organic layer was washed successively with, 100 ml of 2N-hydrochloric acid cooled with ice, 300 ml of saturated sodium thiosulfate, and water until the washings were neutral. The organic layer was dried over anhydrous magnesium sulfate, and the solvent was removed by distillation under reduced pressure. The concentrate was distilled under reduced pressure to obtain 25.3 g (0.135 mol) of o-methoxyphenylbromide.

II )Synthesis of (±)-trans-2-(2-methoxyphenyl)-1-cyclohexanol

A mixture of 3.24 g (0.1 35 mol) of magnesium and 20 ml of tetrahydrofuran was charged into a three-necked flask of 300 ml and stirred. Then, a solution of 25.3 g (0.135 mol) of o-methoxyphenylbromide in 80 ml of tetrahydrofuran was added dropwise at a temperature of 60° C. or less. After the dropping was stopped, the mixture was cooled to −30° C., 0.65g of cuprous chloride was added, and the mixture was stirred for 10 minutes. To the mixture, a solution of 13.3 g (0.135 mol) of cyclohexene oxide in 15 ml tetrahydrofuran was added dropwise. After the dropping was stopped, the temperature was raised to 0° C., and the mixture was stirred for three hours at 0° C. After the temperature was raised to room temperature, the mixture was charged into a separatory funnel and extracted with 600 ml of methylene chloride, and the organic layer was washed with 600 ml of saturated ammonium sulfate. After the organic layer was dried over anhydrous magnesium sulfate, the solvent was distilled away under reduced pressure. The concentrate was distilled under reduced pressure to obtain 17.11 g (0.083 mol ) of (±)-trans-2-(2-methoxyphenyl)-1-cyclohexanol.

III) Optical Resolution of (+)-trans-2-(2-methoxyphenyl)-1-cyclohexanol

A mixture of 10.3 g (0.05 mol) of (+)-trans-2-(2-methoxyphenyl)-1-cyclohexanol, 2.15 g (0,025 mol) of vinyl acetate and 5 ml of toluene was charged into a round bottom flask of 200 ml, 2.6 g of lipase PS powder (manufactured by Amano Pharmaceutical Co., Ltd. )as an esterase was added, and the mixture was stirred for 111 hours at room temperature. The lipase powder was filtered off, the reaction mixture was concentrated under reduced pressure, and 11.5 g of liquid was obtained. Then, the liquid was chromatographed over silica gel (elution with toluene: ethyl acetate =10: I ), and 5.77 g (0.023 mol, yield 46.4%) of (−)-(1R, 2S)-trans-2-(2-methoxyphenyl)-1-acetyloxycyclohexane and 5.38 g (0,026 mol) of (+)-(1S, 2R)-trans-2-methoxyphenyl)-1-cyclohexanol were obtained.

The specific rotation of (−)-(1R, 2S)-trans-2-(2methoxyphenyl)-1-acetyloxycyclohexane was $[\alpha]_D^{34} 1.74°$ (c1.03, MeOH).

The specific rotation of (+)-(1S, 2R)-trans-2-methoxyphenyl)- 1-cyclohexanol was $[\alpha]_D^{34} +54.9°$ (c1.01, MeOH).

Further, (+)-(1S, 2R)-trans-2-(2-methoxyphenyl)-1-cyclohexanol was recrystalized from hexane to obtain 3.33 g (0,016 mol, yield 32.2%, 78.4% ee) of crystals. The specific rotation was $[\alpha]_D^{34} +56.9$ (c 1.06, MeOH).

The optical purity of (+)-(1S, 2R)-trans-2-(2-methoxyphenyl)-1-cyclohexanol was determined by the following method. 0.49 g (0.23 mol) of pyridinium chlorochromate was dissolved in 20 ml of methylene chloride. To the solution, 0.2g (0.01 mol) of (+)-(1S, 2R)-trans-2-(2-methoxyphenyl)-1-cyclohexanol was added dropwise at room temperature, and the mixture was stirred at room temperature for two hours to be oxidized. The reaction solution was concentrated under reduced pressure and chromatographed over silica gel (elution with toluene: ethyl acetate=5:1) to obtain 0.2g (0.01 mol) of (+)-2R, (2-methoxyphenyl)-1-cyclohexanone. The optical purity was determined with a HPLC column for optical resolution (manufactured by Daicel Co., Ltd., CHIRAL CEL OB).

IV) Alcoholysis of (−)-(1R, 2S)-trans-2-(2-methoxyphenyl)-1-acetyloxycyclohexane 5.77 g (0.023 mol) of (−)-(1R, 2S)-trans-2-(2-methoxyphenyl)-1-acetyloxycyclohexane obtained in (III) was refluxed for three hours in a solution of 1.7 g (0.03 mol) of potassium hydroxide in 50 ml of ethanol. After the mixture was cooled to room temperature, 300 ml of diethyl ether was added. The mixture was charged into a separatory funnel, and separated organic layer was washed with 20 ml of 2N-hydrochloric acid cooled with ice and then washed with water until the washings were neutral. The organic layer was dried over anhydrous magnesium sulfate, and the solvent was distilled away under reduced pressure to obtain 4.43 g (0,021 mol) of (−)-(1R, 2S)-trans- 2-(2-methoxyphenyl)-1-cyclohexanol. The specific rotation of the compound obtained was $[\alpha]_D^{28} -62.9°$ (c 1.03, MeOH).

The compound was recrystalized with hexane, and 2.99 g (0,014 g, yield 29%, 99% ee) of white crystals was obtained. The melting point was 40°–42° C. and the specific rotation was $[\alpha]_D^{26} -69.7°$ (c 1.03, MeOH).

The optical purity of (−)-(1R, 2S)-trans-2-(2-methoxyphenyl)-1-cyclohexanol was determined with a HPLC column for optical resolution by introducing into (−)-(1R, 2S) trans-2-(2-methoxyphenyl)-1-cyclohexanone using the same process as described in the case of the above (+)-compound.

EXAMPLE 2

I) Synthesis of o-benzyloxyphenylbromide

Into a three-necked flask of one liter, 25g (0.145 mol) of o-bromophenol, 8.7 g (0.217 mol) of sodium hydroxide and 300 ml of ethanol were charged and refluxed for two hours. Then, 49.4 g (0,289 mol) of benzyl bromide was added dropwise and the mixture was refluxed further for four hours. After the mixture was cooled to room temperature, 600 ml of diethyl ether was added. The mixture was charged into a separatory funnel. Separated organic layer was washed successively with, 100 ml of 2N-hydrochloric acid cooled with ice, 300 ml of saturated sodium thiosulfate, and water until the washings were neutral. The organic layer was dried over anhydrous magnesium sulfate, and the solvent was removed by distillation under reduced pressure. The concentrate was distilled under reduced pressure to obtain 35.6 g (0.135 mol) of o-benzyloxyphenylbromide.

II) Synthesis of (±)-trans-2-(2-benzyloxyphenyl)-1-cyclohexanol

A mixture of 3.24 g (0.1 35 mol) of magnesium and 20 ml of tetrahydrofuran was charged into a three-necked flask of 300 ml and stirred. Then, a solution of 35.6 g of o-benzyloxyphenylbromide in 80 ml of tetrahydrofuran was added dropwise at a temperature of 60° C. or less. After the dropping was stopped, the mixture was cooled to −30° C., 0.65 g of cuprous chloride was added, and the mixture was stirred for 10 minutes. To the mixture, a solution of 13.3 g (0.135 mol ) of cyclohexene oxide in 15 ml tetrahydrofuran was added dropwise at −30° C. After the dropping was stopped. The temperature was raised to 0° C., and the mixture was stirred for three hours at 0° C. After the temperature was raised to room temperature, the mixture was charged into a separatory funnel and extracted with 600 ml of methylene chloride, and the organic layer was washed with 600 ml of saturated ammonium sulfate. After the organic layer was dried over anhydrous magnesium sulfate, the solvent was distilled away under reduced pressure. The concentrate was distilled under reduced pressure to obtain 26.5 g (0,094 mol) of (±)-trans-2-(2-benzyloxyphenyl)-1-cyclohexanol.

III) Optical Resolution of (±)-trans-2-(2-benzyloxyphenyl)-1-cyclohexanol

A mixture of 20 g (0,071 mol) of (+)-trans-2-(2-benzyloxyphenyl)-1-cyclohexanol, 3.1 g (0.036 mol) of vinyl acetate was charged into a round bottom flask of 200 ml, 5 g of lipase PS powder (manufactured by Amano Pharmaceutical Co., Ltd. )as an esterase was added, and the mixture was stirred for 78 hours at room temperature. The lipase powder was filtered off, the reaction mixture was concentrated under reduced pressure, and 20.3 g of liquid was obtained. Then, the liquid was chromatographed over silica gel (elution with toluene: ethyl acetate=10:1), and 9.76 g (0.03 mol, yield 42.4%) of (+)-(1R, 2S)-trans-2-(2-benzyloxyphenyl)-1-acetyloxycyclohexane and 5.38 g (0.026 mol) of (+)-(1S, 2R)-trans-2-benzyloxyphenyl)-1-cyclohexanol were obtained.

The specific rotation of (+)-(1R, 2S)-trans-2-(2-benzyloxyphenyl)-1-acetyloxycyclohexane was $[\alpha]_D^{30}+7.05°$ (c 1.02, MeOH).

The specific rotation of (+)-(1R, 2S)-trans-2-(2-benzyloxyphenyl)-1-cyclohexanol was $[\alpha]_D^{30}+39.9°$ (c 1.02, MeOH).

IV) Alcoholysis of (+)-(1R, 2S)-trans-2-(2-benzyloxyphenyl)-1-acetyloxycyclohexane 9.76 g (0.03 mol) of (+)-(1R, 2S)-trans-2-(2-benzyloxyphenyl)-1-acetyloxycyclohexane obtained in (III) was refluxed for 1 hours in a solution of 2.2g (0.04 mol) of potasium hydroxide in 50 ml of ethanol. After the mixture was cooled to room temperature, 300 ml of diethyl ether was added. The mixture was charged into a separatory funnel, and separated organic layer was washed with 20 ml of 2N-hydrochloric acid cooled with ice and then washed with water until the washings were neutral. The organic layer was dried over anhydrous magnesium sulfate, and the solvent was distilled away under reduced pressure to obtain 8.07 g.

Then, the liquid was chromatographed over silica gel (elution with toluene: ethyl acetate=5:1), and 7.26 g (0.026 mol) of (−)-(1R, 2S)-trans-2-(2-benzyloxyphenyl)-1-cyclohexanol was obtained. The specific rotation of the compound obtained was $[\alpha]_D^{28}-51.9°$ (c 1.06, MeOH).

The effects of the present invention are as follows.

Optically active trans-2-aryl-1-cyclohexanol derivatives of the present invention are new compounds which have been found by the inventors of the present invention. These new compounds are expected to be used as useful asymmetric sources in asymmetric synthesis of physiological active materials and the starting materials.

Using the production process of the present invention, one is enabled to efficiently obtain optically active trans-2-aryl-1-cyclohexanol derivatives of the both enantiomers having high purity in large quantities.

We claim:

1. An optically active trans-2-aryl-1-cyclohexanol derivative represented by the general formula (I):

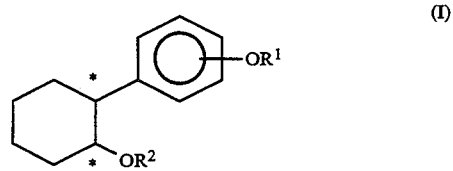

(I)

wherein R¹ is hydrogen, alkyl of 1–15 carbon atoms, methoxymethyl, methoxyethyl, methylthiomethyl, tetrahydropyranyl, cyclopropylmethyl, allyl, cyclohexyl, benzyl, 9-anthrylmethyl or t-butyldimethylsilyl, R² is hydrogen or acyl of 1–15 carbon atoms, and * shows an asymmetric carbon atom.

2. A process for producing optically active trans-2-aryl-1-cyclohexanol compounds comprising reacting a fatty acid vinyl ester or a triglyceride with (±)-trans-2-aryl-1-cyclohexanol represented by the general formula (II):

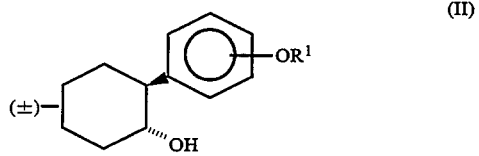

(II)

wherein R¹ is hydrogen, alkyl of 1–15 carbon atoms, methoxymethyl, methoxyethyl, methylthio methyl, tetrahydropyranyl, cyclopropylmethyl, allyl, cyclohexyl, benzyl, 9-anthrylmethyl or t-butyldimethylsilyl) in the presence of an esterase to effect the transesterification reaction and isolating or recovering optically active compound.

* * * * *